United States Patent
Harichian et al.

(10) Patent No.: US 7,659,234 B2
(45) Date of Patent: Feb. 9, 2010

(54) PERSONAL CARE COMPOSITIONS CONTAINING QUATERNARY AMMONIUM TRIHYDROXY SUBSTITUTED DIPROPYL ETHER

(75) Inventors: Bijan Harichian, Brookfield, CT (US); Jose Guillermo Rosa, Shelton, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 638 days.

(21) Appl. No.: 11/557,530

(22) Filed: Nov. 8, 2006

(65) Prior Publication Data

US 2007/0212324 A1      Sep. 13, 2007

Related U.S. Application Data

(60) Provisional application No. 60/779,858, filed on Mar. 7, 2006.

(51) Int. Cl.
C11D 1/62 (2006.01)
C11D 3/43 (2006.01)

(52) U.S. Cl. ............ 510/130; 510/119; 510/123; 510/432; 510/504

(58) Field of Classification Search ............ 424/70, 424/73; 510/119, 123, 130
See application file for complete search history.

(56) References Cited

U.S. PATENT DOCUMENTS

| | | | |
|---|---|---|---|
| 4,663,159 A | 5/1987 | Brode, II et al. | |
| 4,689,217 A | 8/1987 | Restaino et al. | |
| 4,690,817 A | 9/1987 | Davis et al. | |
| 4,775,715 A | 10/1988 | Beresniewicz et al. | |
| 4,978,526 A * | 12/1990 | Gesslein et al. | 424/70.28 |
| 4,994,199 A | 2/1991 | Scardera et al. | |
| 5,698,183 A | 12/1997 | Langer et al. | |
| 5,773,595 A | 6/1998 | Weuthen et al. | |
| 6,290,978 B2 | 9/2001 | Mak et al. | |
| 6,432,907 B1 | 8/2002 | Skold et al. | |
| 6,620,410 B1 | 9/2003 | Cho et al. | |
| 6,649,177 B2 | 11/2003 | Howard et al. | |
| 6,740,317 B1 | 5/2004 | Cho et al. | |
| 6,869,977 B1 | 3/2005 | O'Lenick, Jr. et al. | |
| 2003/0206933 A1 | 11/2003 | Schulze zur Wiesche et al. | |
| 2003/0211952 A1 | 11/2003 | Erazo-Majewicz et al. | |
| 2004/0156877 A1 | 8/2004 | Tokuyama et al. | |
| 2004/0258654 A1 | 12/2004 | Nielsen et al. | |
| 2006/0088496 A1 | 4/2006 | McManus et al. | |
| 2006/0089290 A1 | 4/2006 | Mc Manus et al. | |

FOREIGN PATENT DOCUMENTS

| | | |
|---|---|---|
| DE | 198 35 611 A1 | 8/1998 |
| EP | 0 842 921 A1 | 11/1997 |
| EP | 1 179 339 | 8/2001 |
| EP | 1 366 742 | 12/2003 |
| JP | 63068514 | 3/1988 |
| JP | 1249709 | 10/1989 |
| JP | 05294905 | 4/1992 |
| JP | 9012589 | 1/1997 |
| KR | 10-0656071 | 12/2006 |
| WO | 90/03161 | 4/1990 |
| WO | 96/35410 | 11/1996 |
| WO | 00/61066 | 10/2000 |
| WO | 03/037277 A1 | 5/2003 |

OTHER PUBLICATIONS

Dow—Quat 188 Cationic Monomer: Overview, Jun. 30, 2004.
Arch Personal Care Products Brochure—Honeyquat 50 Substantive Honey Derivative, Jan. 2004.
Arch Personal Care products—In vivo study of moisturizing effects of HoneyQuat 50, Jan. 2004.
Cola Moist 200 Brochure—2004.
Co-Pending Application J6985(C); Harichian et al.; U.S. Appl. No. 11/222,104, filed Sep. 8, 2005.
Co-Pending Application J6986(C); Hurley et al.; U.S. Appl. No. 11/222,189, filed Sep. 8, 2005.

* cited by examiner

*Primary Examiner*—Michael G Hartley
*Assistant Examiner*—Jagadishwar R Samala

(57) ABSTRACT

A personal care composition is provided which includes a trihydroxy and quaternary ammonium substituted dipropyl ether. The substituted dipropyl ether functions as a humectant when applied to human skin to moisturize both in high and low relative humidity environments.

10 Claims, No Drawings

PERSONAL CARE COMPOSITIONS CONTAINING QUATERNARY AMMONIUM TRIHYDROXY SUBSTITUTED DIPROPYL ETHER

BACKGROUND OF THE INVENTION

1. Field of the Invention

The invention concerns personal care compositions providing moisturization both in high and low relative humidity environments.

2. The Related Art

Dry skin is a problem in varying degree to most humans. This condition is particularly evident in winter. Personal care products such as skin creams/lotions, shampoos/conditioners, toilette bars/shower gels and antiperspirant/deodorants are normally formulated with at least one material to address dry skin. Symptoms such as itching flaking and a visually displeasing dermal appearance can all to some extend be modulated.

There are three classes of materials employed against the problem. Occlusives such as petrolatum or silicone oils serve to inhibit loss of natural moisture. They form a barrier between the epidermis and the environment. Another approach is the use of keratolytic agents to enhance rate of dermal exfoliation. Alpha-hydroxy acids are the most common agents for achieving exfoliation.

A third approach to dry skin is topical application of humectants. Hydroxylated monomeric and polymeric organic substances are generally used for this purpose. Glycerin known also as glycerol is one of the most effective humectants.

There are several shortcomings in the performance of known humectants. Even the best such as glycerin requires to be formulated at relatively high levels to achieve good moisturization. Secondly, known humectants perform well in high relative humidity environments; however, hardly any of these substances provide effectiveness at low relative humidity (i.e. less than 20% moisture at 20° C.). Average indoor relative humidity during winter is approximately 13% in areas such as the Northeast U.S. It is quite evident that a real need exists for an improved moisturization technology.

A moisturizer known as Honeyquat 50 with INCI name of Hydroxypropyltrimonium Honey has been reported to be a better humectant than glycerin. See the Arch/Brooks brochure titled "Cosmetic Ingredients & Ideas®", Issue No. 2, August 2001. Honeyquat 50 is described as being derived from the reaction of pendent hydroxyl groups (on the disaccharide) of a "light" deodorized grade of honey with a chlorohydroxytrimethylammonium derivative. Although this substance has excellent humectancy, moisturization at low relative humidity still remains to be conquered.

Accordingly, the present invention seeks to identify humectants which are operative not only at high but also low relative humidity, for application in personal care products.

SUMMARY OF THE INVENTION

A personal care composition is provided which includes:
(i) from about 0.0000001 to about 10% by weight of a quaternized ammonium trihydroxy dipropyl ether selected from the group consisting of formula (I), (II) and mixtures thereof.

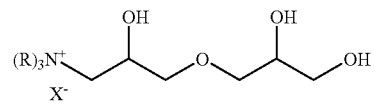

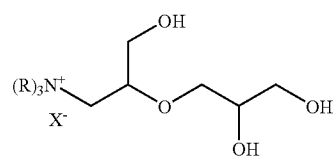

wherein R is the same or different $C_1$-$C_3$ alkyl or hydroxylalkyl group and $X^-$ is a cosmetically acceptable organic or inorganic anion; and
(ii) a cosmetically acceptable carrier.

DETAILED DESCRIPTION OF THE INVENTION

Now it has been found that dipropyl ethers substituted with a quaternary ammonium and three hydroxyl groups are excellent moisturizers providing humectancy in both high and low relative humidity environments. These mono-ethers have the structural formula (I) and (II):

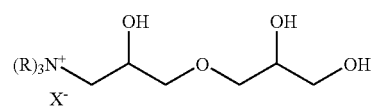

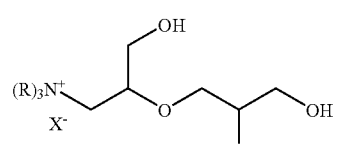

wherein R is the same or different $C_1$-$C_3$ alkyl or hydroxylalkyl group and $X^-$ is a cosmetically acceptable organic or inorganic anion.

Ordinarily the $C_1$-$C_3$ alkyl constituent on the quaternized ammonium group will be methyl, ethyl, n-propyl, isopropyl or hydroxyethyl and mixtures thereof. Particularly preferred is a trimethyl ammonium group known through INCI nomenclature as a "trimonium" group. Any anion can be used in the quat salt. The anion may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, toluoyl sulfate, acetate, citrate, tartrate, lactate, gluconate, and benzenesulfonate. Amounts of these dipropyl ethers may range from about 0.0000001 to about 10%, preferably from about 0.00001 to about 8%, more preferably from about 0.0001 to about 5%, still more preferably from about 0.001 to about 3%, even more preferably from about 0.1 to about 1% by weight of the composition.

Synthesis of the preferred dipropyl ethers (V) and (VI) is achieved by any of the synthetic methods described below: 1) reaction of 2,3-dihydroxypropyl trimethylammonium chloride (III) with 1-chloro-2,3-dihydroxypropane (IV) in the presence of aqueous sodium hydroxide (aq. NaOH) (Scheme 1); 2) treatment of 2,3-dihydroxypropyl trimethylammonium chloride (III) with sodium hydride (NaH) in N,N-dimethylformamide (DMF) or 1-methyl-2-pyrrolidinone (NMP), followed by addition of 1-chloro-2,3-dihydroxypropane (IV) (Scheme II); 3) reaction of 2,3-dihydroxypropyl trimethylammonium chloride (III) with 4-chloromethyl-2,2-dimethyl-1,3-dioxolane (VII) in aqueous basic media, followed by acidification (Scheme III); 4) treatment of 2,2-dimethyl-4-hydroxymethyl-1,3-dioxolane (VIII) with sodium hydride in N,N-dimethylformamide or 1-methyl-2-pyrrolidinone, followed by addition of 1,3-dichloro-2-propanol (IX) and final addition of trimethylamine (X) (Scheme IV). The reaction schemes for the synthetic methods described above are shown below.

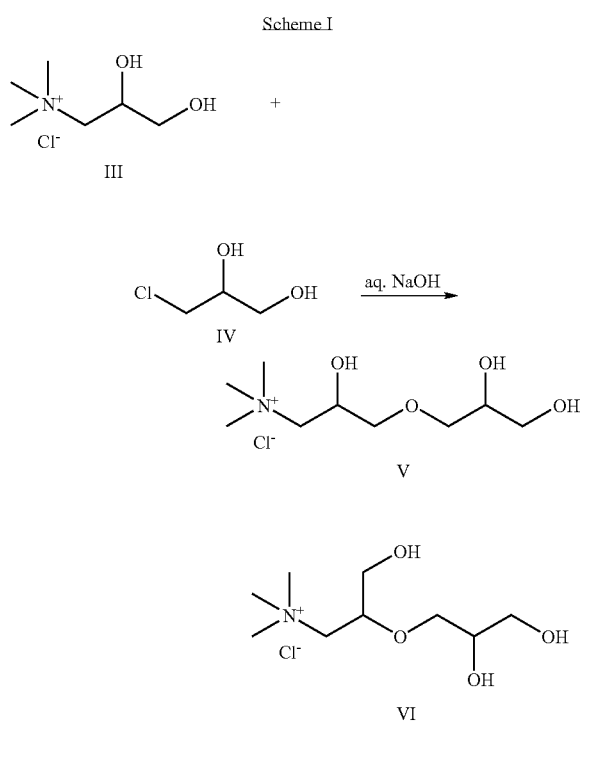

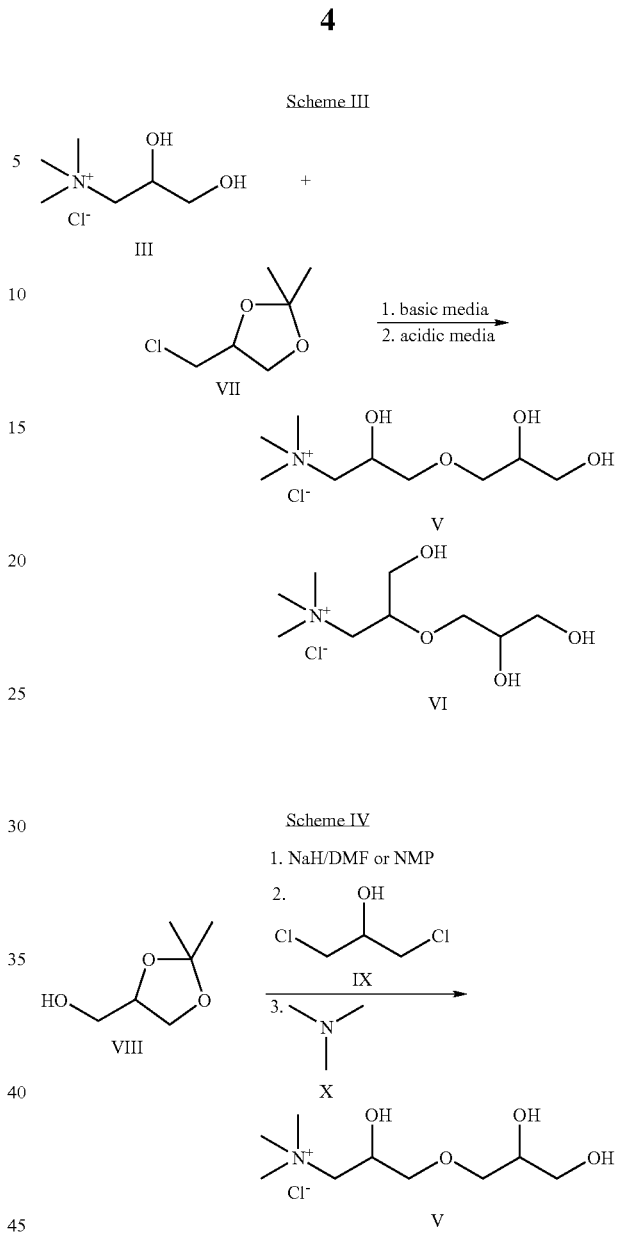

Thus, the present invention also provide new materials as identified by structures (V) and (VI) and a process of manufacture as reported above. The process in its general form reacts 1-chloro-2,3-dihydroxypropane with 2,3-dihydroxypropyl-1-tri($C_1$-$C_3$) ammonium salt in a relative molar ratio ranging from about 3:1 to about 1:3, preferably about 1:1. The reaction is run in the presence of an alkali material which may be sodium hydroxide, potassium hydroxide, lithium hydroxide, calcium oxide, calcium hydroxide or sodium carbonate. The reaction can be run in protic or aprotic medium. Preferably the medium is protic, especially water. Nonetheless, other useful solvents include diethylether, tetrahydrofuran, ethanol, methanol, N,N-dimethylformamide, 1-methyl-2-pyrrolidinone and any mixtures thereof. Alternatively the reaction may be run neat without any solvent. Process temperatures may range from 5° C. to 200° C., with preference given over the range 20 to 50° C.

Advantageously, compositions of the present invention may also include 2,3-dihydroxypropyl tri($C_1$-$C_3$ alkyl or hydroxyalkyl) ammonium salts, the alkyl and salt corresponding to R and X of formula (I) and/or (II). Most preferred for the aforementioned non-ether quat is 2,3-dihydroxypropyl trimethyl ammonium chloride. When the dipropyl ether and non-ether quats are formulated together, they may be present in a weight ratio ranging from about 1:1 to about 1:10,000, preferably from about 1:10 to about 1:5,000, more preferably from about 1:100 to about 1:1,000.

By the term personal care composition is meant any substance applied to a human body for improving appearance, cleansing, odor control or general aesthetics. Nonlimiting examples of personal care compositions include leave-on skin lotions and creams, shampoos, hair conditioners, shower gels, toilet bars, antiperspirants, deodorants, dental products, shave creams, depilatories, lipsticks, foundations, mascara, sunless tanners and sunscreen lotions.

Compositions of this invention will also include a cosmetically acceptable carrier. Amounts of the carrier may range from about 1 to about 99.9%, preferably from about 70 to about 95%, optimally from about 80 to about 90% by weight of the composition. Among the useful carriers are water, emollients, fatty acids, fatty alcohols, thickeners and combinations thereof. The carrier may be aqueous, anhydrous or an emulsion. Preferably the compositions are aqueous, especially water and oil emulsions of the W/O or O/W or triplex W/O/W variety. Water when present may be in amounts ranging from about 5 to about 95%, preferably from about 20 to about 70%, optimally from about 35 to about 60% by weight.

Emollient materials may serve as cosmetically acceptable carriers. These may be in the form of silicone oils, natural or synthetic esters and hydrocarbons. Amounts of the emollients may range anywhere from about 0.1 to about 95%, preferably between about 1 and about 50% by weight of the composition.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 $m^2/s$ at 25° C. Among the preferred nonvolatile emollients useful in the present compositions are the polydimethyl siloxanes having viscosities from about $1 \times 10^{-5}$ to about $4 \times 10^{-4}$ $m^2/s$ at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:

a) Alkyl esters of saturated fatty acids having 10 to 24 carbon atoms. Examples thereof include behenyl neopentanoate, isononyl isonanonoate, isopropyl myristate and octyl stearate.

b) Ether-esters such as fatty acid esters of ethoxylated saturated fatty alcohols.

c) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters, Particularly useful are pentaerythritol, trimethylolpropane and neopentyl glycol esters of $C_1$-$C_{30}$ alcohols.

d) Wax esters such as beeswax, spermaceti wax and tribehenin wax.

e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from about 0.1 to about 20% by weight of the compositions.

Hydrocarbons which are suitable cosmetically acceptable carriers include petrolatum, mineral oil, $C_{11}$-$C_{13}$ isoparaffins, polybutenes, and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, linoleic, linolenic, hydroxystearic and behenic acids.

Fatty alcohols having from 10 to 30 carbon atoms are another useful category of cosmetically acceptable carrier. Illustrative of this category are stearyl alcohol, lauryl alcohol, myristyl alcohol, oleyl alcohol and cetyl alcohol.

Thickeners can be utilized as part of the cosmetically acceptable carrier of compositions according to the present invention, Typical thickeners include crosslinked acrylates (e.g. Carbopol 982®), hydrophobically-modified acrylates (e.g. Carbopol 1382®), polyacrylamides (e.g. Sepigel 305®), acryloylmethylpropane sulfonic acid/salt polymers and copolymers (e.g. Aristoflex HMB® and AVC®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, scierotium, carrageenan, pectin and combinations of these gums. Inorganics may also be utilized as thickeners, particularly clays such as bentonites and hectorites, fumed silicas, talc, calcium carbonate and silicates such as magnesium aluminum silicate (Veegum®). Amounts of the thickener may range from 0.0001 to 10%, usually from 0.001 to 1%, optimally from 0.01 to 0.5% by weight of the composition.

Adjunct humectants may be employed in the present invention. These are generally polyhydric alcohol-type materials. Typical polyhydric alcohols include glycerol, propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of adjunct humectant may range anywhere from 0.5 to 50%, preferably between 1 and 15% by weight of the composition.

Personal care compositions of the present invention may be in any form. These forms may include lotions, creams, roll-on formulations, sticks, mousses, aerosol and non-aerosol sprays and fabric (e.g. nonwoven textile)-applied formulations.

Surfactants may also be present in compositions of the present invention. Total concentration of the surfactant when present may range from about 0.1 to about 90%, preferably from about 1 to about 40%, optimally from about 1 to about 20% by weight of the composition, and being highly dependent upon the type of personal care product. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol, fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) and trialkylamine oxides are also suitable nonionic surfactants.

Preferred anionic surfactants include soap, alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof.

Useful amphoteric surfactants include cocoamidopropyl betaine, $C_{12}$-$C_{20}$ trialkyl betaines, sodium lauroamphoacetate, and sodium laurodiamphoacetate.

Sunscreen agents may also be included in compositions of the present invention. Particularly preferred are such materials as ethylhexyl p-methoxycinnamate, available as Parsol MCX®, Avobenzene, available as Parsol 1789® and benzophenone-3, also known as Oxybenzone. Inorganic sunscreen actives may be employed such as microfine titanium dioxide and zinc oxide. Amounts of the sunscreen agents when present may generally range from 0.1 to 30%, preferably from 2 to 20%, optimally from 4 to 10% by weight of the composition.

Antiperspirants and deodorant compositions of the present invention ordinarily will contain astringent actives. Examples include aluminum chloride, aluminum chlorhydrex, aluminum-zirconium chlorhydrex glycine, aluminum sulfate, zinc sulfate, zirconium and aluminum chlorohydroglycinate, zirconium hydroxychloride, zirconium and aluminum lactate, zinc phenolsulfonate and combinations thereof. Amounts of the astringents may range anywhere from about 0.5 to about 50% by weight of the composition.

Dental products formulated according to the present invention will generally contain a fluoride source to prevent dental caries. Typical anti-caries actives include sodium fluoride, stannous fluoride and sodium monofluoro phosphate. Amounts of these materials will be determined by the amount of fluoride releasable which should range between about 500 to about 8800 ppm of the composition. Other components of dentifrices can include desensitizing agents such as potassium nitrate and strontium nitrate, sweeteners such as sodium saccharine, aspartame, sucralose, and potassium acesulfam. Thickeners, opacifying agents, abrasives and colorants will normally also be present.

Preservatives can desirably be incorporated into the personal care compositions of this invention to protect against the growth of potentially harmful microorganisms. Particularly preferred preservatives are phenoxyethanol, methyl paraben, propyl paraben, imidazoiidinyl urea, dimethyloldimethylhydantoin, ethylenediaminetetraacetic acid salts (EDTA), sodium dehydroacetate, methylchloroisothiazolinone, methylisothiazolinone, iodopropynbutylcarbamate and benzyl alcohol. The preservatives should be selected having regard for the use of the composition and possible incompatibilities between the preservatives and other ingredients. Preservatives are preferably employed in amounts ranging from 0.01% to 2% by weight of the composition.

Compositions of the present invention may include vitamins. Illustrative vitamins are Vitamin A (retinol), Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. For purposes of this invention, vitamins where present are not considered as unsaturated materials. Total amount of vitamins when present in compositions according to the present invention may range from 0.001 to 10%, preferably from 0.01% to 1%, optimally from 0.1 to 0.5% by weight of the composition.

Another type of useful substance can be that of an enzyme such as amylases, oxidases, proteases, lipases and combinations. Particularly preferred is superoxide dismutase, commercially available as Biocell SOD from the Brooks Company, USA.

Skin lightening compounds may be included in the compositions of the invention. Illustrative substances are placental extract, lactic acid, niacinamide, arbutin, kojic acid, ferulic acid, resorcinol and derivatives including 4-substituted resorcinols and combinations thereof. Amounts of these agents may range from about 0.1 to about 10%, preferably from about 0.5 to about 2% by weight of the composition.

Desquamation promoters may be present. Illustrative are the alpha-hydroxycarboxylic acids and beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic acids. Amounts of these materials when present may range from about 0.01 to about 15% by weight of the composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, chamomile, licorice, aloe vera, grape seed, citrus unshui, willow bark, sage, thyme and rosemary.

Also included may be such materials as lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from about 0.000001 to about 10%, preferably from about 0.0001 to about 1% by weight of the composition.

Colorants, opacifiers and abrasives may also be included in compositions of the present invention. Each of these substances may range from about 0.05 to about 5%, preferably between 0.1 and 3% by weight of the composition.

The compositions of the present invention can also be, optionally, incorporated into an insoluble substrate for application to the skin such as in the form of a treated wipe.

A wide variety of packaging can be employed to store and deliver the personal care compositions. Packaging is often dependent upon the type of personal care end-use. For instance, leave-on skin lotions and creams, shampoos, conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered in a stick composition formulation in a container with propel-repel mechanism where the stick moves on a platform towards a dispensing orifice. Metallic cans pressurized by a propellant and having a spray nozzle serve as packaging for antiperspirants, shave creams and other personal care products. Toilette bars may have packaging constituted by a cellulosic or plastic wrapper or within a cardboard box or even encompassed by a shrink wrap plastic film.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

Example 1a

This Example reports the synthesis of 1-trimethylammonium-2,5,6-trihydroxydipropyl ether chloride and 1-trimethylammonium-2-hydroxymethyl-4,5-dihydroxypropyl ethyl ether chloride. To a solution of 2,3-dihydroxypropyl trimethylammonium chloride (500 mg, 2.95 mmol) in aqueous sodium hydroxide (2.95 ml, 2.95 mmol) was added 1-chloro-2,3-dihydroxypropane (247 uL, 2.95 mmol). The resultant solution was stirred at room temperature until the pH decreased to <9 The solution was washed with ether and the aqueous layer evaporated under reduced pressure at 50° C. yielding a heterogeneous colorless syrup. Filtration through glass wool affords an isomeric mixture of 1-trimethylammonium-2,5,6-trihydroxydipropyl ether chloride and 1-trimethylammonium-2-hydroxymethyl-4,5-dihydroxypropyl ethyl ether chloride as a homogeneous syrup: m/z (ESI; $M^+$-$Cl^-$).

Example 1b

This Example reports the synthesis of 1-trimethylammonium-2,5,6-trihydroxydipropyl ether chloride and 1-trimethylammonium-2-hydroxymethyl-4,5-dihydroxypropyl ethyl ether chloride. 2,3-Dihydroxypropyl trimethylammonium chloride (500 mg, 2.95 mmol) is added to a suspension of sodium hydride (2.95 mmol) in N,N-dimethylformamide or 1-methyl-2-pyrrolidone (3-10 ml) and the resulting mixture stirred at room temperature until gas evolution ceases. This mixture is then added to 1-chloro-2,3-dihydroxypropane (247 uL, 2.95 mmol) and the resultant mixture stirred at room temperature until the pH decreases to <9. The solvent is removed under reduced pressure at 50° C. and the residue dissolved in water and washed several times with ether. Removal of the water under reduced pressure at 50° C., followed by filtration through glass wool affords an isomeric mixture of 1-trimethylammonium-2,5,6-trihydroxydipropyl ether chloride and 1 trimethylammonium-2-hydroxymethyl-4,5-dihydroxypropyl ethyl ether chloride as a homogeneous syrup.

Example 1c

This Example reports the synthesis of 1-trimethylammonium-2,5,6-trihydroxydipropyl ether chloride and 1-trimethylammonium-2-hydroxymethyl-4,5-dihydroxypropyl ethyl ether chloride. To a solution of 2,3-dihydroxypropyl trimethylammonium chloride (500 mg, 2.95 mmol) in aqueous sodium hydroxide (2.95 ml, 2.95 mmol) is added 4-chloromethyl-2,2-dimethyl-1,3-dioxolane (418 ul, 2.95 mmol). The resultant solution is stirred at room temperature until the pH decreased to <9 and further washed with ether. Glacial acetic acid (8 ml) is added and the solution stirred room temperature for 16 h. The solution is evaporated under reduced pressure at 50° C. yielding a heterogeneous colorless syrup. Filtration through glass wool affords an isomeric mixture of 1-trimethylammonium-2,5,6-trihydroxydipropyl ether chloride and 1-trimethylammonium-2-hydroxymethyl-4,5-dihydroxypropyl ethyl ether chloride as a homogeneous syrup.

Example 1d

This Example reports the synthesis of 1-trimethylammonium-2,5,6-trihydroxydipropyl ether chloride. 2,2-Dimethyl-4-hydroxymethyl-1,3-dioxolane (367 ul, 2.95 mmol) is added to a suspension of sodium hydride (2.95 mmol) in N,N-dimethylformamide or 1-methyl-2-pyrrolidone (3-10 ml) and the resulting mixture stirred at room temperature until gas evolution ceases. This mixture is then added to 1,3-chloro-2-propanol (281 uL, 2.95 mmol) and the resultant mixture stirred at room temperature until the pH decreases to <9. The solvent is removed under reduced pressure at 50° C. and the residue dissolved in water and washed several times with ether. Removal of the water under reduced pressure at 50° C., followed by filtration through glass wool affords 1-trimethylammonium-2,5,6-trihydroxydipropyl ether chloride as a homogeneous syrup.

Example 2

A representative personal care composition of the present invention in the form of a cosmetic lotion is outlined under Table I.

TABLE I

| INGREDIENT | WEIGHT % |
|---|---|
| PHASE A | |
| Water | Balance |
| Disodium EDTA | 0.05 |
| Methyl Paraben | 0.15 |
| Magnesium Aluminum Silicate | 0.60 |
| Triethanolamine | 1.20 |
| Quaternized Ammonium Trihydroxy Dipropylether Salt of Example 1c | 1.00 |

TABLE I-continued

| INGREDIENT | WEIGHT % |
|---|---|
| PHASE B | |
| Xanthan Gum | 0.20 |
| Natrosol ® 250HHR (ethyl cellulose) | 0.50 |
| Butylene Glycol | 3.00 |
| Glycerin | 2.00 |
| PHASE C | |
| Sodium Stearoyl Lactylate | 0.10 |
| Glycerol Monostearate | 1.50 |
| Stearyl Alcohol | 1.50 |
| Isostearyl Palmitate | 3.00 |
| Silicone Fluid | 1.00 |
| Cholesterol | 0.25 |
| Sorbitan Stearate | 1.00 |
| Butylated Hydroxy Toluene | 0.05 |
| Vitamin E Acetate | 0.01 |
| PEG-100 Stearate | 2.00 |
| Stearic Acid | 3.00 |
| Propyl Paraben | 0.10 |
| Parsol MCX ® | 2.00 |
| Caprylic/Capric Triglyceride | 0.50 |
| Hydroxycaprylic Acid | 0.01 |
| C12-15 Alkyl Octanoate | 3.00 |
| PHASE D | |
| Vitamin A Palmitate | 0.10 |
| Bisabolol | 0.01 |
| Vitamin A Acetate | 0.01 |
| Fragrance | 0.03 |
| Retinol 50C | 0.02 |
| Conjugated Linoleic Acid | 0.50 |

Example 3

A water-in-oil topical liquid make-up foundation according to invention is described in Table II below.

TABLE II

| INGREDIENT | WEIGHT % |
|---|---|
| PHASE A | |
| Cyclomethicone | 9.25 |
| Oleyl Oleate | 2.00 |
| Dimethicone Copolyol | 20.00 |
| PHASE B | |
| Talc | 3.38 |
| Pigment (Iron Oxides) | 10.51 |
| Spheron L-1500 (Silica) | 0.50 |
| PHASE C | |
| Synthetic Wax Durachem 0602 | 0.10 |
| Arachidyl Behenate | 0.30 |
| PHASE D | |
| Cyclomethicone | 1.00 |
| Trihydroxystearin | 0.30 |
| PHASE E | |
| Laureth-7 | 0.50 |
| Propyl Paraben | 0.25 |
| PHASE F | |
| Fragrance | 0.05 |
| PHASE G | |
| Water | balance |
| Quaternized Ammonium Trihydroxy Dipropylether Salt of Example 1a | 3.00 |
| Methyl Paraben | 0.12 |

TABLE II-continued

| INGREDIENT | WEIGHT % |
|---|---|
| Propylene Glycol | 8.00 |
| Niacinamide | 4.00 |
| Glycerin | 3.00 |
| Sodium Chloride | 2.00 |
| Sodium Dehydroacetate | 0.30 |

Example 4

Illustrated herein is a skin cream incorporating a dipropyl ether salt of the present invention and a non-ether quat.

TABLE III

| INGREDIENT | WEIGHT % |
|---|---|
| Glycerin | 6.93 |
| Niacinamide | 5.00 |
| 2,3-Dihydroxypropyl Trimethyl Ammonium Chloride | 5.00 |
| Permethyl 101A[1] | 3.00 |
| Sepigel 305[2] | 2.50 |
| Q2-1403[3] | 2.00 |
| Linseed Oil | 1.33 |
| Arlatone 2121[4] | 1.00 |
| Cetyl Alcohol CO-1695 | 0.72 |
| SEFA Cottonate[5] | 0.67 |
| Tocopherol Acetate | 0.50 |
| Panthenol | 0.50 |
| Stearyl Alcohol | 0.48 |
| Titanium Dioxide | 0.40 |
| Quaternized Ammonium Trihydroxy Dipropylether Salt of Example 1a | 0.10 |
| Disodium EDTA | 0.10 |
| Glydant Plus[6] | 0.10 |
| PEG-100 Stearate | 0.10 |
| Stearic Acid | 0.10 |
| Purified Water | Balance |

[1]Isohexadecane, Presperse Inc., South Plainfield, NJ
[2]Polyacrylamide (and) C13-14 Isoparaffin (and) Laureth-7, Seppic Corporation, Fairfield, NJ
[3]dimethicone (and) dimethiconol, Dow Corning Corp. Midland, MI
[4]Sorbitan Monostearate and Sucrococoate, ICI Americas Inc., Wilmington, DE
[5]Sucrose ester of fatty acid
[6]DMDM Hydantoin (and) Iodopropynyl Butylcarbamate, Lonza Inc., Fairlawn, NJ Example 5

Illustrative of another cosmetic composition incorporating a dipropyl ether salt according to the present invention is the formula of Table IV.

TABLE IV

| INGREDIENT | WEIGHT % |
|---|---|
| Polysilicone-11 | 29 |
| Cyclomethicone | 59 |
| Petrolatum | 11 |
| Quaternized Ammonium Trihydroxy Dipropylether Salt of Example 1a | 0.2 |
| Dimethicone Copolyol | 0.3 |
| Sunflowerseed Oil | 0.5 |

Example 6

A relatively anhydrous composition incorporating a dipropyl ether salt of the present invention is reported in Table V.

TABLE V

| INGREDIENT | WEIGHT % |
|---|---|
| Cyclomethicone | 80.65 |
| Dimethicone | 9.60 |
| Squalane | 6.00 |
| Isostearic Acid | 1.90 |
| Borage Seed Oil | 0.90 |
| Quaternized Ammonium Trihydroxy Dipropylether Salt of Example 1b | 0.50 |
| Retinyl Palmitate | 0.25 |
| Ceramide 6 | 0.10 |
| Tocopherol | 0.10 |

Example 7

An aerosol packaged foaming cleanser with a dipropyl ether salt suitable for the present invention is outlined in Table VI.

TABLE VI

| INGREDIENT | WEIGHT % |
|---|---|
| Sunflower Seed Oil | 20.00 |
| Maleated Soybean Oil | 5.00 |
| Silicone Urethane | 1.00 |
| Polyglycero-4 Oleate | 1.00 |
| Sodium C14-16 Olefin Sulfonate | 15.00 |
| Sodium Lauryl Ether Sulphate (25% active) | 15.00 |
| Cocoamidopropylbetaine | 15.00 |
| DC 1784 ® (Silicone Emulsion 50%) | 5.00 |
| Polyquaternium-11 | 1.00 |
| Quaternized Ammonium Trihydroxy Dipropylether Salt of Example 1b | 1.00 |
| Water | Balance |

Example 8

A disposable, single use personal care towelette product is described according to the present invention. A 70/30 polyester/rayon non-woven towelette is prepared with a weight of 1.8 grams and dimensions of 15 cm by 20 cm. Onto this towelette is impregnated a composition with a dipropyl ether salt as outlined in Table VII below.

TABLE VII

| INGREDIENT | WEIGHT % |
|---|---|
| 2,3-Dihydroxy Trimethyl Ammonium Chloride | 5.00 |
| Glycerin | 2.00 |
| Hexylene Glycol | 2.00 |
| Disodium Capryl Amphodiacetate | 1.00 |
| Gluconolactone | 0.90 |
| Silicone Microemulsion | 0.85 |
| Witch Hazel | 0.50 |
| PEG-40 Hydrogenated Castor Oil | 0.50 |
| Fragrance (Terpenoid Mixture) | 0.20 |
| Quaternized Ammonium Trihydroxy Dipropylether Salt of Example 1c | 0.05 |
| Vitamin E Acetate | 0.001 |
| Water | Balance |

Example 9

A toilette bar illustrative of the present invention is outlined under Table VIII.

TABLE VIII

| INGREDIENT | WEIGHT % |
|---|---|
| Sodium Soap (85/15 Tallow/Coconut) | 77.77 |
| Quaternized Ammonium Trihydroxy Dipropylether Salt of Example 1a | 3.50 |
| Glycerin | 2.50 |
| Sodium Chloride | 0.77 |
| Titanium Dioxide | 0.40 |
| Fragrance | 1.50 |
| Disodium EDTA | 0.02 |
| Sodium Etidronate | 0.02 |
| Fluorescer | 0.024 |
| Water | Balance |

Example 10

A shampoo composition useful in the context of the present invention is described in Table IX below.

TABLE IX

| Ingredient | Weight % |
|---|---|
| Ammonium Laureth Sulfate | 12.00 |
| Ammonium Lauryl Sulfate | 2.00 |
| Cocoamidopropyl Betaine | 2.00 |
| Sodium Lauroamphoacetate | 2.00 |
| 2,3-Dihydroxypropyl Trimethyl Ammonium Chloride | 1.50 |
| Ethylene Glycol Distearate | 1.50 |
| Cocomonoethanolamide | 0.80 |
| Cetyl Alcohol | 0.60 |
| Polyquaternium-10 | 0.50 |
| Quaternized Ammonium Trihydroxy Dipropylether Salt of Example 1a | 0.50 |
| Dimethicone | 1.00 |
| Zinc Pyridinethione | 1.00 |
| Sodium Citrate | 0.40 |
| Citric Acid | 0.39 |
| Sodium Xylene Sulfonate | 1.00 |
| Fragrance | 0.40 |
| Sodium Benzoate | 0.25 |
| Kathon CG ® | 0.0008 |
| Benzyl Alcohol | 0.0225 |
| Water | Balance |

Example 11

This Example illustrates an antiperspirant/deodorant formula incorporating the moisturizing actives according to the present invention.

TABLE X

| Ingredient | Weight % |
|---|---|
| Cyclopentacycloxane | 44 |
| Dimethicone | 20 |
| Aluminum Zirconium Trichlorohydrex Glycinate | 15 |
| Quaternized Ammonium Trihydroxy Dipropylether Salt of Example 1c | 5.0 |
| $C_{18}$-$C_{36}$ Acid Triglyceride | 5.0 |
| Microcrystalline Wax | 3.0 |
| Glycerin | 3.0 |
| Silica | 2.5 |
| Dimethicone Crosspolymer | 1.0 |
| Fragrance | 0.5 |

TABLE X-continued

| Ingredient | Weight % |
| --- | --- |
| Disodium EDTA | 0.4 |
| Butylated Hydroxytoluene | 0.3 |
| Citric Acid | 0.3 |

Example 12

A toothpaste according to the present invention can be formulated with the ingredients listed under Table XI.

TABLE XI

| Ingredients | Weight % |
| --- | --- |
| Zeodent 115 ® | 20.00 |
| Glycerin | 18.00 |
| Xanthan Gum | 7.00 |
| Sodium Carboxymethyl Cellulose | 0.50 |
| Sodium Bicarbonate | 2.50 |
| Quaternized Ammonium Trihydroxy Dipropylether Salt of Example 1a | 2.00 |
| Sodium Laurylsulfate | 1.50 |
| Sodium Fluoride | 1.10 |
| Sodium Saccharin | 0.40 |
| Titanium Dioxide | 1.00 |
| Pluronic F-127 ® | 2.00 |
| FD&C Blue No. 1 | 3.30 |
| Menthol | 0.80 |
| Potassium Nitrate | 5.00 |
| Water | balance |

Example 13

A moisturizing oil-in-water lotion can be formulated with the ingredients listed under Table XII.

TABLE XII

| INGREDIENT | WEIGHT % |
| --- | --- |
| Water | Balance |
| Quaternary Ammonium Trihydroxydipropylether Salt of Example 1c | 0.5 |
| Glycerin | 5.00 |
| Disodium EDTA | 0.1 |
| Methylparaben | 0.1 |
| Niacinamide | 0.5 |
| Triethanolamine | 0.25 |
| D-Panthenol | 0.1 |
| Sodium Dehydroacetate | 0.1 |
| Benzyl Alcohol | 0.25 |
| GLW75CAP-MP (75% aq. TiO2 Dispersion)[1] | 0.5 |
| Hexamidine Disethionate | 0.1 |
| Palmitoyl-Pentapeptide[2] | 0.0003 |
| N-Acetyl Glucosamine | 1.0 |
| Soy Isoflavone | 0.5 |
| Isohexadecane | 3.0 |
| Isopropyl Isostearate | 0.5 |
| Cetyl Alcohol | 0.3 |
| Stearyl Alcohol | 0.35 |
| Behenyl Alcohol | 0.3 |
| PEG-100 Stearate | 0.1 |
| Cetearyl Glucoside | 0.1 |
| Sodium Acrylate/Sodium Acryloyldimethyl Tuarate Copolymer/Isohexadecane/Polysorbate 80 | 3.0 |
| Dimethicone/Dimethiconol | 1.0 |

TABLE XII-continued

| INGREDIENT | WEIGHT % |
| --- | --- |
| Polymethylsilsequioxane | 0.5 |
| Timiron Splendid Red[3] | 1.0 |

[1]Available from Kobo products
[2]Palmitoyl-lysine-threonine-threonine-lysine-serine available from Sederma
[3]Silica and titanium dioxide coated mica red interference pigment available from Rona Example 14

Illustrated herein is a moisturizing water-in-silicone cream/lotion formulated with the ingredients listed under Table XIII

TABLE XIII

| INGREDIENT | WEIGHT % |
| --- | --- |
| Water | Balance |
| Quaternary Ammonium Trihydroxydipropylether Salt of Example 1a | 0.5 |
| Allantoin | 0.2 |
| Disodium EDTA | 0.1 |
| Ethyl Paraben | 0.2 |
| Propyl Paraben | 0.1 |
| Caffeine | 1.0 |
| BHT | 0.1 |
| Dexpanthenol | 0.5 |
| Glycerin | 10.0 |
| Niacinamide | 2.0 |
| Palmitoyl-Pentapeptide[1] | 0.0003 |
| GLW75CAP-MP (75% aq. TiO2 Dispersion)[2] | 0.5 |
| Timiron Splendid Red[3] | 1.0 |

[1]Palmitoyl-lysine-threonine-threonine-lysine-serine available from Sederma
[2]GLW75CAP-MP, 75% aqueous titanium dioxide dispersion from Kobo
[3]Silica and titanium dioxide coated mica red interference pigment available from Rona

What is claimed is:

1. A personal care composition comprising:
   (i) from about 0.0000001 to about 10% by weight of a quaternized ammonium trihydroxy dipropyl ether selected from the group consisting of formula (I), (II) and mixtures thereof

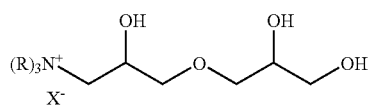

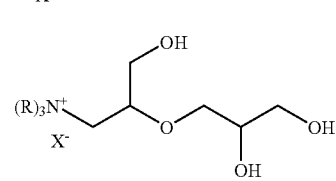

wherein R is the same or different $C_1$-$C_3$ alkyl or hydroxylalkyl group and $X^-$ is a cosmetically acceptable organic or inorganic anion; and
   (ii) a cosmetically acceptable carrier.

2. The composition according to claim 1 wherein R is a methyl group.

3. The composition according to claim 1 wherein $X^-$ is chloride.

4. The composition according to claim 1 further comprising a 2,3-dihydroxypropyl tri($C_1$-$C_3$) quaternary ammonium salt.

5. The composition according to claim 4 wherein the ratio of dipropyl ether to quaternary ammonium salt ranges from 1:1 to about 1:10,000 by weight.

6. The composition according to claim 5 wherein the ratio ranges from about 1:10 to about 1:5,000 by weight.

7. The composition according to claim 5 wherein the ratio ranges from about 1:100 to about 1:1,000.

8. The composition according to claim 4 wherein the quaternary ammonium salt is 2,3-dihydroxypropyl trimethylammonium chloride.

9. A compound having the formula (I) or (II)

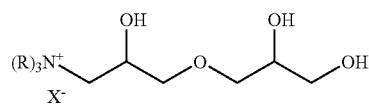

I

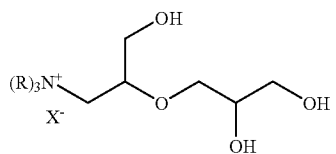

II wherein R is the same or different $C_1$-$C_3$ alkyl or hydroxylalkyl group and $X^-$ is a cosmetically acceptable organic or inorganic anion.

10. A compound according to claim 9 wherein R is methyl and $X^-$ is chloride.

* * * * *